United States Patent [19]

Nehen et al.

[11] Patent Number: 5,635,211

[45] Date of Patent: Jun. 3, 1997

[54] MICROCAPSULES HAVING WALLS MADE OF POLYISOCYANATE/GUANIDINE REACTION PRODUCTS

[75] Inventors: Ulrich Nehen, Leverkusen; Jürgen Weisser, Dormagen, both of Germany

[73] Assignee: Bayer Aktiengesellschaft, Leverkusen, Germany

[21] Appl. No.: 391,990

[22] Filed: Feb. 21, 1995

[30] Foreign Application Priority Data

Jan. 19, 1995 [DE] Germany ............... 195 01 479.0

[51] Int. Cl.⁶ ............... B01J 13/02; C08G 18/38; B41M 5/165
[52] U.S. Cl. ............... 424/489; 424/490; 424/497; 424/501; 428/402.2; 428/402.21; 428/402.22; 264/4.1; 264/4.33; 264/4.7; 503/200; 503/215
[58] Field of Search .................... 424/489, 490, 424/497, 501; 428/402.2, 402.21, 402.22; 264/4.1, 4.33, 4.7; 503/200, 215

[56] References Cited

U.S. PATENT DOCUMENTS 4,804,687  2/1989  Weimann et al. .................. 521/53

*Primary Examiner*—Nathan M. Nutter
*Attorney, Agent, or Firm*—Sprung Horn Kramer & Woods

[57] ABSTRACT

Novel microcapsules are characterized in that their walls are made of reaction products of guanidine compounds and polyisocyanates or contain such reaction products. Dispersions containing such microcapsules can be prepared by replacing the amines, amino alcohols or hydrazine compounds in processes known per se for preparing microcapsule dispersions from polyisocyanates and amines, amino alcohols or hydrazine compounds by guanidine compounds. The present invention also relates to no-carbon copy papers containing dyestuff precursors in microcapsules whose walls are made of reaction products of guanidine compounds and polyisocyanates or contain such reaction products.

9 Claims, No Drawings

MICROCAPSULES HAVING WALLS MADE OF POLYISOCYANATE/GUANIDINE REACTION PRODUCTS

The present invention relates to microcapsules having walls made of polyisocyanate/guanidine reaction products, to the production thereof and to improved copy papers containing such microcapsules.

Microcapsules having walls made of polyurea or polyurea/polyurethane are usually prepared by a two-phase polyaddition process. To this end, an oil phase containing an organic water-immiscible inert solvent, polyisocyanate and the material to be encapsulated is emulsified in an aqueous phase containing water and, if desired, additives such as emulsifiers, stabilizers and/or materials for preventing coalescence. The addition of a polyamine or an amino alcohol to this emulsion initiates a polyaddition reaction of amino and/or hydroxyl groups with isocyanate groups at the interface between oil droplets and water phase. As a result thereof, the oil droplets are enveloped by a polyurea or polyurea/polyurethane wall. This gives a dispersion of microcapsules containing the material to be encapsulated and the organic solvent. The size of the microcapsules is approximately equal to the size of the emulsified oil droplets.

Water can also take part in the polyaddition reaction, for example by hydrolysing isocyanate groups to give amino groups which can then react with any isocyanate groups still present.

The relative amounts of reactants for the polyaddition are in general selected in such a manner that any isocyanate groups present are reacted.

Polyisocyanates which can be used include a wide range of difunctional and higher functional isocyanates having an aliphatic or aromatic structure and polyamines which can be used include a wide range of amines of aliphatic structure containing two or more $NH_2$ groups per molecule. Hydrazine, hydrazine derivatives and/or amino alcohols containing at least one $NH_2$ and at least one OH group per molecule can also be used.

Known microencapsulation methods are described, for example, in EP-A 227,562, DE-A 3,620,347, DE-A 3,635,823, Japanese Patent Application 231,377 of 14.09.1987, EP-A 392,876 and US-A 5,164,216.

It has also been suggested to use salts of polyamines. The addition of alkali to these salts produces free amines capable of undergoing polyaddition reactions (see, for example, JP-A2 42,77,027).

The most important area in which microcapsules are used is the production of no-carbon copy papers. In this case, the microcapsules contain a dyestuff precursor. The act of writing destroys the microcapsules in those places where sufficient pressure is applied. The discharged dyestuff precursor upon making contact with a developer produces an image of the writing. The intensity of this image and the rate at which the dyestuff precursor produces the image are dependent, inter alia, on the mechanical and chemical nature of the capsule wall and are frequently not completely satisfactory.

The hitherto used polyamines and amino alcohols are prepared via organochloro intermediates. Their preparation and handling requires a certain amount of additional effort in order to ensure ecological safety. Hydrazine compounds as such are toxic and therefore also require additional measures during handling.

Microcapsules have now been found which are characterized in that their walls are made of reaction products of guanidine compounds and polyisocyanates or contain such reaction products.

In contrast to organic amines, the parent compound guanidine is available from low-cost and readily handlable inorganic raw materials, that is lime, coke and nitrogen, without the use of elemental chlorine (see, for example, Ullmanns Encyclopädie der technischen Chemie 4th Edition, Weinheim 1975, Volume 9, pages 70 and 642, Volume 10, page 146 and Volume 12, page 411).

The microcapsules prepared according to the invention by means of polyisocyanates and guanidine compounds, when used in practice for no-carbon copy papers, usually result in a higher copy intensity than microcapsules prepared from polyisocyanates and di- or polyamines in accordance with the prior art. This property of microcapsules according to the invention in combination with the ecologically favourable raw material base is a particular advantage in practical applications.

Examples of guanidine compounds which are suitable for preparing the microcapsules according to the invention are those of the formula (I)

$$H_2N-\underset{\underset{X}{\|}}{C}-NHY, \quad (I)$$

in which
X represents HN=,

Y represents H—, NC—, $H_2N$—, HO—,

and salts thereof with acids.

For example, the salts can be salts of carbonic acid, nitric acid, sulphuric acid, hydrochloric acid, silicic acid, phosphoric acid, formic acid and/or acetic acid. Salts of guanidine compounds of the formula (I) can be used in combination with inorganic bases in order to obtain the free guanidine compounds of the formula (I) in situ from the salts. Examples of inorganic bases which are suitable for this purpose are alkali metal hydroxides and/or alkaline earth metal hydroxides and/or alkaline earth metal oxides. Preference is given to aqueous solutions or slurries of these bases, in particular to aqueous sodium hydroxide solution, aqueous potassium hydroxide solution and aqueous solutions or slurries of calcium hydroxide. Combinations of a plurality of bases can also be used.

It is often advantageous to use the guanidine compounds of the formula (I) as salts because they are commercially available in this form and some of the free guanidine compounds are sparingly soluble in water or are not stable on storage. If inorganic bases are used, they can be employed in stoichiometric, less than stoichiometric and more than stoichiometric amounts, relative to the salts of guanidine compounds. It is preferred to use 10 to 100 equivalent % of inorganic base (relative to the salts of guanidine compounds). The addition of inorganic bases has the effect that during microencapsulation guanidine compounds having free $NH_2$ groups are available in the aqueous phase for the reaction with the polyisocyanates present in the oil phase. During microencapsulation, the addition of salts of guanidine compounds and of bases is advantageously carried out such that they are added separately to the aqueous phase.

Preference is given to the use of guanidine or salts of guanidine with carbonic acid, nitric acid, sulphuric acid, hydrochloric acid, silicic acid, phosphoric acid, formic acid and/or acetic acid.

It is particularly advantageous to use salts of guanidine compounds with weak acids. In aqueous solution these salts are, as a result of hydrolysis, in equilibrium with the corresponding free guanidine compound. The free guanidine compound is consumed during the encapsulation process but is constantly regenerated in accordance with the law of mass action. This advantage is especially observed with guanidine carbonate. When salts of guanidine compounds with weak acids are used, no inorganic bases for releasing the free guanidine compounds need to be added.

The guanidine compounds of the formula (I) which are suitable for the present invention can be prepared by ion exchange from their water-soluble salts by prior art methods using commercially available basic ion exchangers. The eluate from the ion exchanger can be used directly for producing the capsule wall by mixing it with the oil-in-water emulsion.

For example, the amount of guanidine compounds used can be such that for each mol of NCO groups present in the oil phase as polyisocyanate 0.2 to 4.0 mol of free $NH_2$ groups in the form of guanidine compounds are introduced into the water phase or released there. Preferably, this amount is 0.5 to 1.5 mol. If the guanidine compounds are used in less than a stoichiometric amount, free NCO groups remain after the reaction with the polyisocyanate. In general, these groups then react with water which is usually not critical since new free amino groups capable of crosslinking are formed.

Preferably, the guanidine compounds are used in the form of aqueous solutions. The concentration of such solutions is not critical and is in general only limited by the solubility of the guanidine compounds in water. For example, 1 to 20% strength by weight aqueous solutions of guanidine compounds are suitable.

The polyisocyanates which can be used for producing the microcapsules according to the invention include a wide range of aliphatic, aromatic and aromatic-aliphatic difunctional and higher functional isocyanates, in particular those known for producing microcapsules. It is preferred to use aliphatic polyisocyanates. The following are used particularly preferably: hexamethylene diisocyanate, isophorone diisocyanate and/or derivatives of hexamethylene diisocyanate and of isophorone diisocyanate having free isocyanate groups and containing biuret, isocyanurate, uretdione and/or oxadiazinetrione groups. Mixtures of different polyisocyanates can also be used. Some useful polyisocyanates are described, for example, in EP-A 227,562, EP-A 164,666 and EP-A 16,378.

The microcapsules according to the invention are preferably used for producing no-carbon copy papers. Accordingly, they preferably contain a dyestuff precursor as the encapsulated material. Suitable for this purpose are dyestuff precursors of a wide range of types, in particular triphenylmethane compounds, diphenylmethane compounds, bisindolylphthalide compounds, bisarylcarbazolylmethane compounds, xanthene compounds, benzoxazine compounds, thiazine compounds and spiropyran compounds, in particular those known as dyestuff precursors for producing no-carbon copy papers. Mixtures of a plurality of dyestuff precursors can also be used. Some useful dyestuff precursors are described, for example, in EP-A 591,106, EP-A 315,901, EP-A 234,394, DE-A 3,622,262 and EP-A 187,329.

Examples of organic, water-immiscible and inert solvents which together with the material to be encapsulated and the polyisocyanate form part of the oil phase during production of the microcapsules include aromatic, aliphatic and naphthenic hydrocarbons, carboxylic esters, chlorinated paraffins, oils of animal and vegetable origin, natural fats having melting points in the range from 10° to 35° C. and aromatic and aliphatic ethers boiling above 100° C. Mixtures of a plurality of solvents can also be used.

When producing the microcapsules according to the invention, the aqueous phase may contain emulsifiers, stabilizers and/or materials for preventing coalescence. If desired, the oil phase may also contain emulsifiers. The amount of such additives can, for example, range from 0 to 2% by weight, relative to the particular phase.

Microcapsules according to the invention can contain not only dyestuff precursors but also, for example, perfume oils, scents, adhesives, pharmaceuticals, insecticides, fungicides, herbicides and repellents. It is to be understood that the materials to be encapsulated must not react with isocyanates under the encapsulation conditions.

Microcapsules according to the invention can be produced by continuous and batchwise methods known per se, in which case the crosslinking agents to be used are not the customary polyamines but guanidine compounds. Specifically, guanidine compounds of the formula (I) or salts thereof, possibly in combination with inorganic bases, are used. The use of basic salts of guanidine compounds with weak acids also gives good results. From a technical point of view, this procedure is particularly advantageous since the free base does not have to be prepared separately, for example by addition of inorganic bases or by ion exchange.

Not only the preparation of the emulsion containing droplets of an oil phase and a continuous aqueous phase but also the addition of guanidine compounds can be carried out continuously or batchwise.

The batchwise procedure can be such, for example, that a guanidine compound is added to an emulsion containing oil droplets having approximately the size of the desired microcapsules at 10° to 50° C. in such an amount as is required stoichiometrically for the reaction of all isocyanate groups present in the oil phase. If guanidine compounds are available as salts, first an aqueous solution of the particular salt can, if desired, be run through an anion exchanger to give an aqueous solution of the free guanidine compound which is then used. It is assumed that all $NH_2$ groups present in guanidine compounds or obtained from salts of guanidine compounds are capable of reacting with NCO groups. It is assumed that one mole of guanidine and guanidine salts (formula (I), X is NH, Y is H) can react with 2 mol of NCO groups.

The contact between free guanidine compounds and polyisocyanates present in the oil phase initiates a polyaddition reaction at the interfaces between the oil droplets and the aqueous phase which is also called crosslinking. This reaction can, if desired, be completed at elevated temperature, for example up to the boiling point of the aqueous phase. This gives a dispersion of microcapsules in water, the capsule content of which can be up to about 60% by weight. Capsule content is understood to mean the weight ratio of oil phase, including the isocyanate, to aqueous phase in the starting emulsion. When calculating the capsule content, the guanidine compound which participates in the wall formation and any inorganic base used are not taken into account.

Salts of guanidine compounds can also be added to the abovementioned emulsion. In this case, the temperature is maintained below 60° C., and an inorganic base of the type described can then be added, preferably in a stoichiometric amount, relative to the salt. This leads to an in-situ release of guanidine compounds which then react in the abovementioned manner. In the case of salts of guanidine compounds with weak acids which are cleaved hydrolytically in the presence of water and then contain portions of free guanidine compounds, the addition of inorganic bases can be omitted. This is true in particular of guanidine carbonate.

The continuous procedure can be such, for example, that an emulsion of the desired type and oil droplet size is produced continuously in an emulsifying machine by the flow-through method. This can be followed by continuous addition of an aqueous solution of a guanidine compound and, if desired, in a downstream reaction vessel, if necessary, of the inorganic base required for releasing guanidine compounds from salts, for example at 25° to 50° C., without applying shear forces. The polyaddition reaction can then be completed in other reaction vessels, if desired at temperatures of up to 100° C.

The microcapsules according to this invention possess a number of advantages. They have good mechanical and chemical stability, rapidly produce an intensive image of the writing when used for no-carbon copy papers and are prepared using guanidine compounds available on an industrial scale and preparable from the building blocks lime, coke and nitrogen in a simple and low-cost manner requiring little expenditure.

The present invention also provides a process for preparing microcapsule dispersions in which an oil phase containing an organic, water-immiscible inert solvent, the material to be encapsulated and a polyisocyanate is emulsified in a water phase containing, if desired, additives, and adding to the emulsion a substance which is capable of undergoing addition reactions with isocyanate groups, which process is characterized in that a guanidine compound is added to the emulsion.

Finally, the present invention also provides no-carbon copy papers which contain dyestuff precursors in microencapsulated form and are characterized in that the walls of the microcapsules contain reaction products of guanidine compounds with polyisocyanates.

What has been said above with respect to the microcapsules according to the invention applies accordingly to the process according to the invention for preparing microcapsule dispersions and to the no-carbon copy paper according to the invention.

EXAMPLES

Percentages are by weight unless stated otherwise.

EXAMPLE 1 a) Preparation of a microcapsule dispersion

To prepare microcapsules for use in the art of no-carbon copy papers, first an oil phase was prepared by dissolving a dyestuff precursor mixture consisting of 15 g of crystal violet lactone, 7.5 g of a blue-developing dyestuff of the bisarylcarbazolylmethane type (Pergascript® Blue S-RB) and 2.5 g of a red-developing dyestuff precursor of the bisindolyphthalide type (Pergascript® Red I6B) at 120° C. in 975 g of diisopropylnaphthalene, and adding 40 g of 1,3,5-tris-(6-isocyanatohexyl) isocyanurate (NCO content 21.5%) to 360 g of this solution of room temperature. This oil phase was combined with 521.9 g of a water phase consisting of a 1% strength by weight aqueous polyvinyl alcohol solution, the resulting mixture was stirred to give a coarse preemulsion which was emulsified for 8 minutes using a mixing siren (8,950 rpm) to give a fine emulsion. 74.2 g of an 8.15% strength aqueous guanidine solution was added to the fine emulsion obtained at room temperature, the resulting mixture was heated to 60° C. over a period of 1 hour with stirring, and stirring at this temperature was continued for 3 hours. This gave an approximately 40% strength microcapsule dispersion whose microcapsules had an average size of 7.8 µm.

b) Production of a no-carbon copy paper 12.9 g of the microcapsule dispersion obtained by a), 2.05 g of a cellulose-based spacer (Arbocell® BE600/30), 2.01 g of a binder based on a styrene/butadiene latex (Baystal® P KA8588) and 26.3 g of deionized water were mixed, and the resulting mixture was knife-coated (40µ) onto the back of a commercially available CF paper and dried by means of a stream of hot air. (CF paper is a coated front paper, i.e. a paper to the top side of which a developer for dyestuff precursors has been applied.) This gave a CFB paper containing 5.5 g/m$^2$ of a layer containing the microencapsulated dyestuff precursors, the spacer and the binder. (CFB paper denotes a coated front and back paper, that is a paper to the top side of which a developer for dyestuff precursors and to the bottom side of which a microencapsulated dyestuff precursor have been applied.) The CFB paper was placed on another CF paper in such a manner that the developer layer of the CF paper and the dyestuff precursor layer of the CFB paper made contact. A compressive force set at 600N was applied to the CF side of the CFB paper using a pressure-testing device (IGT Tester A1), resulting in a blue printed copy on the CF paper. Its colour intensity was determined by means, of a McBeth densitometer. A value of 0.44 was obtained (the greater the number, the more intensive the colour of the printed copy).

EXAMPLE 2

40 g of the oxadiazinetrione of hexamethylene diisocyanate (NCO content 20.6%—prepared by the method of DE-A 1,670,664) was added to 360 g of an oil phase prepared according to Example 1, and the resulting mixture was treated with 454.4 g of 1% strength aqueous polyvinyl alcohol solution as described in Example 1 to give an oil-in-water emulsion. A solution consisting of 11.9 g of guanidine nitrate, 3.9 g of sodium hydroxide and 123.5 g of water was added to the resulting emulsion at room temperature, and the mixture was heated to 60° C. over a period of 3 hours and stirred at 60° C. for another 4 hours. This gave a dispersion having a capsule content of about 41% and an average particle size of 7.4 µm which, after being brush-coated onto paper and measured (as described in Example 1) produced a printed copy having an intensity value of 0.55.

EXAMPLE 3

The procedure as described in Example 1 was repeated. However, the polyisocyanate described there was replaced by 40 g of a hexamethylene diisocyanate trimer having a biuret structure and an NCO content of 23.4%. The oil phase and 482 g of a polyvinyl alcohol solution (1% strength in water) were used to produce an oil-in-water emulsion under a high shear rate, and the resulting emulsion was converted at room temperature into a capsule dispersion by adding a solution of 13.6 g of guanidine nitrate, 4.5 g of sodium hydroxide and 118 g of water. Ripening of the dispersion was achieved by 4 hours of slow stirring at 60° C. The resulting capsule dispersion had an average particle diameter of 7.7 μm and a capsule content of 40%. After being brush-coated onto paper and measured (as described in Example 1) it produced a printed copy having an intensity value of 0.54.

EXAMPLE 4

40 g of the oxadiazinetrione of hexamethylene diisocyanate (NCO content 20.6%—prepared by the method of DE-A 1,670,664) was added to 360 g of the oil phase described in Example 1, and the resulting mixture was treated with 506 g of aqueous 1% strength polyvinyl alcohol solution as described to give an oil-in-water emulsion. In parallel a solution of 9.4 g of guanidine carbonate in 84.7 g of water was prepared and then added dropwise at a temperature of 50° C. to the oil-in-water emulsion with slow stirring. During this addition, the pH of the mixture was constantly measured and the rate of dropwise addition adjusted in such a way that the pH remained between 8 and 9. Stirring at 60° C. was then continued for 1 hour. The resulting dispersion had a capsule content of about 40% and an average particle size of 7.0 μm. After being brush-coated onto paper and measured (as described in Example 1) it produced a printed copy having an intensity value of 0.62.

EXAMPLE 5

The procedure of Example 3 was repeated, except that guanidine nitrate was replaced by guanidine carbonate, no sodium hydroxide solution was used, and the amount of isocyanate was reduced.

Guanidine carbonate: 70.0 g of a 10% strength solution in water

Isocyanate: 28 g of the biuret of hexamethylene diisocyanate, NCO content 23.4%

Colouring solution: 372 g, same type as described in Example 1

Water phase: 537 g of 1% strength aqueous polyvinyl alcohol solution

After addition of the guanidine carbonate solution at room temperature, the dispersion was heated to 58° C. over a period of 1 hour and stirred at this temperature for another 4 hours. This gave an approximately 40% strength microcapsule dispersion having an average particle size of 6.0 μm. The copying characteristics were tested as in Example 1 and the intensity value obtained was 0.51.

EXAMPLE 6

380 g of a colouring solution prepared as described in Example 1 was mixed with 20 g of a polyisocyanate consisting predominantly of the uretdione of hexamethylene diisocyanate having an NCO content of 22.5%. After addition of 55.6 g of 1% strength aqueous polyvinyl alcohol solution, an oil-in-water emulsion was prepared under a high shear rate, the droplet size of the emulsion corresponding to that of the desired capsule. A solution of 4.8 g of guanidine carbonate in 43.3 g of water was added at room temperature to this emulsion with careful stirring, and the mixture was heated to 80° C. over a period of 75 minutes. After 4 hours of stirring at this temperature, the resulting capsule dispersion was analysed. It gave the following values:

average capsule diameter: 8.1 μm
capsule content: 40.8%
intensity value: 0.54 (determined as described in Example 1).

EXAMPLE 7

40 g of a polyisocyanate mixture having an NCO content of 22.1% and consisting of 20% of the oxadiazinetrione and of 80% of the uretdione of hexamethylene diisocyanate was added to 360 g of a colouring solution prepared as described in Example 1. After addition of 544.5 g of a 1% strength aqueous polyvinyl alcohol solution, an emulsion was prepared under a high shear rate. A solution consisting of 6.4 g of guanidine nitrate, 2.1 g of sodium hydroxide and 55.5 g of water was added to this emulsion at room temperature with careful stirring. The temperature of the dispersion was then increased to 58° C. over a period of 60 minutes with stirring, and stirring at this temperature was continued for 4 hours. The resulting dispersion had a capsule content of about 40% and an average capsule diameter of 6.9 μm. The intensity value measured as in Example 1 was 0.52.

EXAMPLE 8

40 g of a polyisocyanate obtained by reacting isocyanurate-containing hexamethylene diisocyanate trimer with polyether alcohol (by the method of EP-A 206,059) and having an NCO content of 19.5% was added to 360 g of a colouring solution prepared as described in Example 1. This mixture and 554 g of a 1% strength aqueous polyvinyl alcohol solution were treated under a reduced shear rate but otherwise as described in Example 1 to give an emulsion. Its conversion into a capsule dispersion was effected at room temperature by adding 51 g of a 10% strength guanidine solution in water prepared by ion exchange of a guanidine carbonate solution on a basic ion exchanger. The resulting dispersion was aftertreated as described in Example 7. Its analysis showed a capsule content of about 41%, an average capsule diameter of 9.9 μm and an intensity value of 0.40 (measured as in Example 1).

EXAMPLE 9

28 g of a hexamethylene diisocyanate trimer of biuret structure (NCO content 23.4%) was added to 372 g of an oil phase prepared as described in Example 1, and the resulting mixture was treated as described in Example 1 with 494 g of an aqueous 1% strength polyvinyl alcohol solution to give an oil-in-water emulsion. A slurry consisting of 10.6 g of aminoguanidine carbonate in 95.4 g of water was added at room temperature to the emulsion obtained with slow stirring. The temperature of the mixture was then increased to 60° C. over a period of 60 minutes. During this time, the pH was continuously controlled and maintained in the range from 8 to 9 by appropriate addition of 20% strength aqueous sodium hydroxide solution. Stirring at 60° C. was continued for 4 hours. The resulting dispersion had a capsule content of about 41% and an average particle size of 6.5 μm. After being brush-coated onto paper and measured as described in Example 1 it gave an intensity value of 0.42. The density test (carded out as in Example 10) showed that dense capsules were present.

EXAMPLE 10

25 g of crystal violet lactone and 975 g of a mixture of diisopropylnaphthalene isomers were made at 100° C. into a 2.5% strength clear solution 720 g of which, after cooling, were weighed in a beaker, 80 g of the isocyanurate of hexamethylene diisocyanate (Desmodur® N 3300, NCO content 21.5%) was added, and the resulting mixture was homogenized. 1100 g of a 1% strength aqueous polyvinyl alcohol (polyvinyl alcohol of the AIRVOL® 523 type) was added to this solution, and the resulting mixture was treated by high-speed stirring using an anchor stirrer to give a coarse preemulsion. The high-speed emulsifying treatment was continued using a high-speed mixing siren (9000 rpm) until the oil droplets had been broken down to droplet sizes of 7 µm. The emulsion was divided into two portions of 950 g each.

A solution of 7.0 g of diethylenetriamine in 71 g of deionized water was added to the first portion at room temperature and with slow stirring, and a solution of 6.0 g of guanidine in 68 g of deionized water was added to the second portion in an analogous manner. The resulting dispersions were heated to 60° C. over a period of 2 hours and after reaching this temperature slow stirring was continued for another 4 hours.

The capsule dispersions were then characterized and analysed as follows:

|  | Capsule dispersion prepared with diethylenetriamine | Capsule dispersion prepared with guanidine |
|---|---|---|
| Capsule content determined by drying at 150° C. to constant weight | about 40% | about 39% |
| Average capsule diameter | 7.4 µm | 7.7 µm |
| Viscosity measured in a Brookfield viscometer at room temperature | 105 mPa.s | 120 mPa.s |
| Density (dense means that after mixing with dilute silica sol solution no discolouration can be detected, brushcoated onto base paper and dried at 70° C. for 2 hours) | dense | dense |
| Intensity value (determined as described in Example 1) | 0.39 | 0.44 |
| Writing intensity (a paper coated with 2 g of capsules/m² was placed with the capsule side on a paper coated with a developer, the letter "W" was typed on the top side of the capsule paper of both papers in an electric typewriter and the printed copy produced on the developer side was measured by a reflectometer (Elrephomat Zeiss-Jena). Higher numerical values indicate a more intensive image) | 31.2 | 33.9 |

The above table shows that capsules according to the invention (prepared with guanidine) are superior with respect to the intensity values and image intensities to be obtained to capsules prepared by the prior art method (with diethylenetriamine). The remaining properties and measured values do not differ significantly in the two capsule types.

We claim:

1. Microcapsules, characterized in that their walls are made of reaction products of guanidine compounds of the formula (I)

in which

X represents HN=,

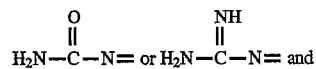

Y represents H—, NC—, $H_2N$—, HO—,

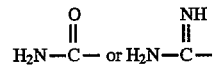

or salts thereof with acids and polyisocyanates or contain such reaction products.

2. Microcapsules according to claim 1, characterized in that the salts are salts of carbonic acid, nitric acid, sulphuric acid, hydrochloric acid, silicic acid, phosphoric acid, formic acid and/or acetic acid.

3. Microcapsules according to claim 1, characterized in that salts of guanidine compounds and 10 to 100 equivalent % of inorganic bases (relative to the salts of guanidine compounds) are used in preparing them.

4. Microcapsules according to claim 1, characterized in that for each mole of NCO groups in the polyisocyanate 0.2 to 4.0 mol of free $NH_2$ groups in the form of guanidine compounds are introduced or released in preparing them.

5. Microcapsules according to claim 1, characterized in that the polyisocyanates used in preparing them are hexamethylene diisocyanate, isophorone diisocyanate and/or derivatives of hexamethylene diisocyanate and of isophorone diisocyanate having free isocyanate groups and containing biuret, isocyanurate, uretdione and/or oxadiazinetrione groups.

6. Microcapsules according to claim 1, characterized in that they contain dyestuff precursors and water-immiscible and inert solvents which are aromatic, aliphatic and/or naphthenic hydrocarbons, carboxylic esters, chlorinated paraffins, oils of animal and vegetable origin, natural fats having melting points in the range from 10° to 35° C. and/or aromatic or aliphatic ethers boiling above 100° C.

7. Microcapsules according to claim 1, characterized in that they were obtained batchwise at 10° to 50° C. by adding a guanidine compound in such an amount as is required stoichiometrically for the reaction of all isocyanate groups present or were prepared continuously at 25° to 50° C. by adding an aqueous solution of a guanidine compound and, if desired, releasing guanidine compounds from salts using an inorganic base.

8. Microcapsules and no-carbon copy papers according to claim 1, characterized in that the guanidine compound used is guanidine carbonate and that no inorganic base is used.

9. A copy paper which does not contain carbon which comprises dyestuff precursors encapsulated in microcapsules according to claim 1.

* * * * *